United States Patent [19]
Kobayashi et al.

[11] Patent Number: 6,156,492
[45] Date of Patent: Dec. 5, 2000

[54] ADSORBENT CARRIER CONTAINING IMMOBILIZED SULFATED POLYSACCHARIDE AND LIGAND FOR DIRECT HEMOPERFUSION

[75] Inventors: Akira Kobayashi, Settsu; Satoshi Takata, Takasago, both of Japan

[73] Assignee: Kaneka Corporation, Osaka, Japan

[21] Appl. No.: 09/202,664

[22] PCT Filed: May 30, 1997

[86] PCT No.: PCT/JP97/01868

§ 371 Date: Dec. 18, 1998

§ 102(e) Date: Dec. 18, 1998

[87] PCT Pub. No.: WO97/48428

PCT Pub. Date: Dec. 24, 1997

[30] Foreign Application Priority Data

Jun. 21, 1996 [JP] Japan .................................. 8-161925

[51] Int. Cl.[7] .............................. A01N 1/02; C12N 11/10; B01D 15/00; A61M 37/00; C08B 37/00
[52] U.S. Cl. ............................. 435/2; 210/660; 435/178; 435/179; 530/415; 536/18.7; 536/21; 536/56; 536/112; 536/114; 536/122; 536/20; 604/5
[58] Field of Search ................................ 435/174, 2, 178, 435/179; 536/17.5, 4.1, 54, 73, 74, 118, 124, 18.7, 20, 21, 56, 112, 114, 122; 210/660; 530/415; 604/5

[56] References Cited

U.S. PATENT DOCUMENTS

| | | | |
|---|---|---|---|
| 5,116,962 | 5/1992 | Stuber et al. | 525/54.2 |
| 5,324,823 | 6/1994 | Asakawa et al. | 530/415 |
| 5,401,415 | 3/1995 | Rauh et al. | 210/660 |

FOREIGN PATENT DOCUMENTS

| | | |
|---|---|---|
| 59-196738 | 11/1984 | Japan . |
| 5-168707 | 7/1993 | Japan . |
| 08052303 | 2/1996 | Japan . |

*Primary Examiner*—David M. Naff
*Attorney, Agent, or Firm*—Armstrong, Westerman, Hattori, McLeland & Naughton

[57] ABSTRACT

An adsorbent for use in direct hemoperfusion to adsorb and remove harmful substances from blood is prepared by immobilizing a sulfated polysaccharide and/or its salt on a water-insoluble carrier. Preferably, the sulfated polysaccharide has a limiting viscosity of 0.005 to 0.5 dl/g and a sulfur content of 5 to 22% by weight, and is immobilized on the carrier in an amount of 0.02 to 200 mg per ml of carrier. Carrier particles can have an average particle size of 30 to 5000 μm, and preferably 120 to 800 μm. The sulfated polysaccharide inhibits adhesion of hemocytes and exhibits an anticoagulation property to extend blood coagulation time, and has additional functions of adsorbing releasing factors released from hemocytes, adsorbing lipoproteins, and enabling reduction of carrier particle size to about 30 μm. Immobilizing a ligand on the carrier with the sulfated polysaccharide makes it possible to adsorb and remove specific substances in blood that bind to the ligand.

13 Claims, No Drawings

ADSORBENT CARRIER CONTAINING IMMOBILIZED SULFATED POLYSACCHARIDE AND LIGAND FOR DIRECT HEMOPERFUSION

TECHNICAL FIELD

The present invention relates to a carrier for an adsorbent used for direct hemoperfusion and a method for minimizing a particle size of the same.

BACKGROUND ART

It has been known that an adsorbent prepared by immobilizing a ligand on a carrier is used to adsorb and remove harmful substances from blood. For such adsorption and removal, there is a method of continuously treating blood by perfusion of it. As the perfusion method, there are a method of separating blood into a hemocyte (hemocyte component) and plasma component and treating only the plasma component by adsorption and removal, and a direct hemoperfusion method for subjecting the whole blood to adsorption and removal treatment without separating the hemocyte and plasma component.

In general in order to enhance an adsorption efficiency, particle sizes of an adsorbent and a carrier therefor may be decreased to increase an effective surface area. This way of thinking can be realized in, for example, a batch treatment and an adsorption treatment of only the plasma component having a low viscosity and containing no hemocyte without so much difficulty as the direct hemoperfusion method.

On the other hand in the direct hemoperfusion method for treating the whole blood, a method of passing the whole blood through a column filled with an adsorbent (also called on-line method) has been adopted generally. Besides that method, there is a method of putting an adsorbent sparsely in a blood bag, mixing the adsorbent with blood to conduct an adsorption treatment, and then filtrating the adsorbent and returning the blood to a patient (bag method). In any of the methods, since the whole blood contacts directly to a foreign material, i.e. the adsorbent, there occur adhesion, breakage and activation of hemocytes, for example, platelets, etc. and activation of a blood coagulating system, and thus the blood tends to coagulate. This phenomenon is greatly affected by material and particle size of a carrier for an adsorbent and appears significantly particularly as the particle size decreases. Therefore though it was known that an adsorption efficiency is increased by using an adsorbent having a smaller particle size, it has been considered that in the direct hemoperfusion method, minimizing the particle size of the adsorbent was difficult from the viewpoint of securing a stable flow of blood. Particularly in case of the on-line method, if adhesion and aggregation of hemocytes occur, a blood passage is not secured and there arises a problem with the flow of blood. From these points of view, at present a carrier for an adsorbent which has an average particle size exceeding about 400 μm is used.

In the bag method, flow of blood does not come into question particularly, and an adsorbent having a smaller particle size as compared with the on-line method can be used. However even in such a case, when the particle size becomes smaller, the above-mentioned adhesion of hemocytes and coagulation of blood are caused. Thus there is a limit in minimizing the particle size.

As mentioned above, an adsorbent used for the direct hemoperfusion for treating the whole blood cannot always be satisfactory merely by making the particle size smaller. It is important that the adhesion of hemocytes, etc. can be inhibited.

An object of the present invention is to minimize the particle size of a carrier used for the direct hemoperfusion with maintaining excellent flow of blood.

The present inventors have made intensive studies with respect to similarity to heparin, toxicity, interaction with a hemocyte and protein, and the like of a sulfated polysaccharide, and as a result, have found that when a carrier is modified with a sulfated polysaccharide or its salt, even if a particle size of the carrier for direct hemoperfusion is further minimized, high passage of hemocytes is exhibited, activation thereof is inhibited and a coagulation time of blood is not shortened, and thus have completed the present invention.

DISCLOSURE OF THE INVENTION

Namely the present invention relates to the carrier for an adsorbent which is used for direct hemoperfusion and is prepared by immobilizing a sulfated polysaccharide and/or its salt on a water-insoluble carrier, and to the method for minimizing a particle size of the carrier.

BEST MODE FOR CARRYING OUT THE INVENTION

A sulfated polysaccharide and/or its salt used in the present invention do not activate hemocytes and thus do not cause obstruction in passing blood such as coagulation of blood. Besides that, the sulfated polysaccharide and/or its salt have a function of adsorbing and catching releasing factors (factors causing an overresponse to an organism, i.e. biologically active amines such as serotonin and histamine, basic polypeptides such as platelet factor 4 (PF4) and β-thromboglobulin (βTG), proteins having affinity with heparin such as thrombospondin and fibronectin, neutral protease such as granulocytic elastase, and the like), and are useful also as a ligand.

A limiting viscosity of the sulfated polysaccharide or its salt which is immobilized on the water-insoluble carrier is preferably not less than 0.005 dl/g and not more than 0.5 dl/g from the viewpoint of inhibiting adhesion of hemocytes, more preferably not less than 0.007 dl/g and not more than 0.4 dl/g from the viewpoint of conducting the immobilizing further efficiently, particularly not less than 0.008 dl/g and not more than 0.2 dl/g from the viewpoint of inhibiting nonspecific adsorption of plasma components in addition to the above-mentioned advantages.

A sulfur content of the sulfated polysaccharide or its salt is preferably not less than 5% by weight and not more than 22% by weight from the viewpoint of inhibiting adhesion of hemocytes, more preferably not less than 8% by weight and not more than 22% by weight from the viewpoint of anticoagulation property, particularly not less than 13% by weight and not more than 22% by weight from the viewpoint of inhibiting adhesion of hemocytes further stably and exhibiting anticoagulation property.

An amount of the sulfated polysaccharide or its salt to be immobilized on the water-insoluble carrier is preferably not less than 0.02 mg and not more than 200 mg per 1 ml of the water-insoluble carrier from the viewpoint of inhibiting adhesion of hemocytes and exhibiting anticoagulation property, more preferably not less than 0.1 mg and not more than 100 mg from the viewpoint of inhibiting excessive anticoagulation property, particularly not less than 0.5 mg and not more than 40 mg from practical point of view and from the viewpoint of excellent effect of inhibiting adhesion of hemocytes and exhibiting anticoagulation property.

Thus it is preferable from the point of securing flow of blood to immobilize the sulfated polysaccharide and/or its salt having a limiting viscosity of not less than 0.005 dl/g and not more than 0.5 dl/g and a sulfur content of not less than 5% by weight and not more than 22% by weight, on the water-insoluble carrier in an amount of not less than 0.02mg and not more than 200 mg per 1 ml of the water insoluble carrier.

Representative examples of the sulfated polysaccharide or its salt suitable for the use in the present invention are, for instance, sulfated polysaccharides such as heparin, dextran sulfate, chondroitin sulfate, chondroitin polysulfate, heparan sulfate, keratan sulfate, heparin sulfate, xylan sulfate, caronin sulfate, chitin sulfate, chitosan sulfate, cellulose sulfate, agarose sulfate, agaropectin sulfate, pectin sulfate, inulin sulfate, arginine sulfate, glycogen sulfate, polylactose sulfate, carrageenin sulfate, starch sulfate, polyglucose sulfate, laminarin sulfate, galactan sulfate, levan sulfate and mepesulfate, potassium salt and sodium salt thereof, and the like. The sulfated polysaccharide or its salt used in the present invention are not limited to them. From the viewpoints of production cost and availability of starting materials, the most preferable examples are heparin, dextran sulfate and chondroitin polysulfate.

In the present invention, the carrier, the particle size of which can be minimized may be water-insoluble and may be in a soft gel or hard gel. Examples of the carrier in a soft gel are, for instance, dextran, agarose, polyacrylamide and the like. However since pressure resistance is desired (a degree of consolidation is low) from the viewpoint of the use for direct hemoperfusion, the hard gel is more preferred. Among the hard gels, a polymer hard gel is preferred from the points that a porous article can be obtained relatively easily and that a water-swelling property is low. Examples of the polymer hard gel in the present invention are a synthetic high molecular compound such as polymethyl methacrylate, polyvinyl alcohol, styrene-divinylbenzene copolymer, cross-linked polyvinyl alcohol, cross-linked polyacrylate, cross-linked vinyl ether- maleic anhydride copolymer, cross-linked styrene-maleic anhydride copolymer or cross-linked polyamide, a hard porous article using a natural high molecular compound such as cellulose as a starting material, an inorganic porous article such as porous glass or porous silica gel, and the like. The surface of the above-mentioned inorganic porous articles may be coated with a polysaccharide, synthetic high molecular compound, or the like. Those polymer hard gels may be used alone or in an admixture of two or more thereof. However in the present invention, the hard gels are not limited to them.

A hard gel is distinguished from a soft gel by the following method. That is, when a relation between flow rate and pressure-drop is determined by uniformly packing a gel in a cylindrical glass column (inner diameter: 9 mm, column length: 150 mm) provided with filters having a pore size of 15 $\mu$m at both ends of the column and passing an aqueous liquid through the column, a hard gel shows a nearly linear relationship, while in case of a soft gel, a gel is deformed and consolidated when its pressure exceeds a certain point so that a flow rate does not increase further. In the present invention, when the above-mentioned column is used, a gel having the above linear relationship up to at least 0.3 kg/cm$^2$ is referred to as a hard gel.

The carrier is in the granular form and may be somewhat deformed. According to the method of the present invention, the carrier can be minimized considerably (particle size: about 30 $\mu$m). In the bag method, in order to securely separate the adsorbent from the blood after the adsorbing treatment, a carrier having an average particle size of not less than 30 $\mu$m is preferred. In case where a carrier is used for the on-line method of direct hemoperfusion, when a lower limit of an average particle size is less than 80 $\mu$m, there is a case where the hemoperfusion becomes difficult due to individual difference. Though an upper limit of an average particle size of the carrier is not particularly limited, the average particle size is preferably not more than 5000 $\mu$m from the viewpoint of adsorbing performance. From the viewpoints of stable direct hemoperfusion and adsorbing performance in the on-line method, the average particle size is more preferably not less than 100 $\mu$m and not more than 1000 $\mu$m, particularly preferably not less than 120 $\mu$m and not more than 800 $\mu$m. To carry out the direct hemoperfusion stably and not to activate hemocytes carelessly and release releasing factors, it is important in the present invention to limit an average particle size distribution of the particles. A too wide average particle size distribution causes adhesion and activation of hemocytes, and a too narrow distribution tends to inhibit physical adhesion and activation due to turbulent flow. Therefore in the present invention, it is preferred that a particle size of the carrier particles amounting to not less than 80% by volume of the carrier particles is distributed within ±75% of the average particle size, more preferably within ±50% in order to inhibit the activation of hemocytes by the adsorbing apparatus itself and efficiently adsorb and remove the releasing factors from the hemocytes, particularly preferably within ±25%.

The method of the present invention is to immobilize the above-mentioned sulfated polysaccharide and/or its salt on the water-insoluble carrier. Besides a known coating method, there are immobilizing methods such as physical adsorption method, ionic coupling methods and covalent coupling methods. The method of the present invention is not limited to them. Though research and development of various synthetic high molecular materials having anti-thrombogenic property have been made actively, polysaccharides are safer than those materials. However since it is not preferred that the sulfated polysaccharide is flowed into a living body, the covalent coupling method, in which the bond is strong and difficult to be un-bonded, is more preferred. Also since it is important that the sulfated polysaccharide is not released at the time of sterilizing, from this point of view, the covalent coupling method assuring strong bond is desirable. Even when an ionic coupling method is used, it is desirable to cross-link the sulfated polysaccharide by covalent coupling. Particularly it is possible to inhibit interaction with proteins and hemocytes by introducing a spacer between the carrier and the sulfated polysaccharide.

In immobilizing a sulfated polysaccharide, it is desirable that a functional group capable of reacting easily with the sulfated polysaccharide exists on a surface of the carrier. Representative examples of such a functional group are, for instance, an amino group, carboxyl group, hydroxyl group, thiol group, acid anhydride group, succinylimide group, chlorine atom, aldehyde group, amide group, epoxy group and the like. These functional groups are introduced, if necessary, to the carrier by known method. Examples of the method for immobilizing by covalent coupling are, for instance, methods employing cyanogen halide, epichlorohydrin, bisepoxide, triazine halide, and the like. Among them, a method employing epichlorohydrin is most preferable because bond is particularly strong and there is less possibility of separation of the sulfated polysaccharide.

The method of the present invention is one utilizing a function for inhibiting adhesion of hemocytes and a function for extending a blood coagulation time, which a sulfated polysaccharide or its salt possesses. Therefore if a ligand for a specific purpose is immobilized on a carrier having a particle size minimized by the method of the present invention, it is possible to adsorb and remove specific substances in blood efficiently with maintaining a good flow of blood. For immobilizing a ligand, known method can be used. Examples of such a ligand are (1) substances having affinity with a specific substance derived from an organism, for instance, immunoglobulin, fragment thereof such as Fab', Fab' and F(ab')$_2$, glucosaminoglucan such as heparin, saccharides, and the like; (2) (poly)anion and (poly)cation substances which exhibit affinity by an electrostatic interaction, for instance, substances having an anionic group such as a carboxyl group, sulfonic acid group, sulfuric acid group or phosphoric acid group or substances having a cationic group such as an amino group or substituted amino group; (3) substances exhibiting affinity by a hydrophobic interaction, for instance, substances having a long chain alkyl group, aromatic group, silicon compound or fluorine compound; and the like. The ligand is not limited to them.

The adsorbent using the carrier of the present invention can be used on any of the above-mentioned bag method and on-line method. The method is not limited to them, and the adsorbent is applicable to any direct hemoperfusion methods, in which the whole blood is treated and is returned into a body of a patient after the adsorption treatment.

As mentioned above, the sulfated polysaccharide or its salt per se used in the present invention has a function of adsorbing and catching releasing factors released from hemocytes, for example, biologically active amines such as serotonin and histamin; basic polypeptides such as platelet factor 4, β-thromboglobulin, platelet derived growth factor (PDGF) and basic fibroblast growth factor (bFGF); proteins having affinity with heparin such as thrombospondin, fibronectin and epidermal growth factor (EGF); factors causing an overresponse to an organism such as neutral proteases, i.e. granulocyte elastase and the like; and lipoproteins in blood such as LDL and VLDL. Therefore the carrier for an adsorbent which is obtained in the present invention is solely useful as an adsorbent for adsorbing and removing the above-mentioned releasing factors and lipoproteins through direct hemoperfusion method even without immobilizing a ligand.

The method of the present invention is then explained below by means of examples, and the present invention is not limited to them.

In the following examples, an interaction between the hemocyte and the carrier having a minimized particle size which was prepared by the method of the present invention and a fluctuation of a blood coagulation time were studied for evaluation of flow of blood in the direct hemoperfusion. Usually when blood contacts to a foreign material which does not exist in blood, a hemocyte immediately adheres to a surface of the foreign material and a blood coagulation system is activated. Therefore it is suitable to use these interaction and fluctuation as indices for evaluating the interaction between the carrier and the blood. In examples, the results of the interaction with hemocytes are shown by a percentage of passed hemocytes (%) and a percentage of non-adhered platelets (%). In any cases, 100% is an upper limit, and it means that the higher the percentage is, the weaker the interaction between the various carriers and the hemocytes is. With respect to the blood coagulation time, two kinds of coagulation times were measured, i.e. a coagulation time of an intrinsic pathway which is easy to reflect an influence of contact to a foreign material and a coagulation time of extrinsic pathway to be activated by a tissue factor. The blood coagulation time which is not changed or is extended (in view of inhibiting coagulation by contact to a foreign material) by contact to a carrier is preferred more than the coagulation time which is shortened by an activation due to contact to a carrier. Also in Examples of the present invention, when the coagulation time is shorter than that at the time of collecting blood, it shows that the blood is easy to coagulate, and compatibility with a carrier is judged to be low. On the contrary, when the coagulation time is not changed or tends to extend, the compatibility can be judged to be higher in that the blood is not in a state of easily coagulated.

EXAMPLE 1

To twenty milliliters of a porous cellulose gel (available from Chisso Corporation, average particle size: 80 μm, not less than 80% by volume of particles have a particle size of within ±10% of an average particle size) in sedimentation volume was added 20 ml of reverse osmosis water (RO water, Yamato Pure Line RO 21 available from Yamato Kagaku Kabushiki Kaisha), followed by heating to raise an inside temperature to 40° C. To the mixture was added 11 ml of 2M NaOH and shaking was carried out at 40° C. for 30 minutes. Then thereto was added 3.6 ml of epichlorohydrin, followed by reaction at 40° C. for two hours. After the completion of reaction, a gel was washed with about two liters of RO water to give an epoxidated gel. An amount of introduced epoxy groups was 13 μmol/g.

To fifteen milliliters of the epoxidated gel in sedimentation volume was added a solution prepared by dissolving 10.5 g of dextran sulfate (molecular weight: about 2,000, limiting viscosity: 0.012 dl/g, sulfur content: 13% by weight) in 19 ml of reverse osmosis water, and stirring was conducted. Then pH of the mixture solution was adjusted to 10 with 2N NaOH, followed by reaction at 45° C. for 24 hours to carry out immobilization of the dextran sulfate.

RO water was added to 115 μl of monoethanolamine to give a solution having a total amount of 3.3 ml. The aqueous solution was added to the previously prepared gel (sedimentation volume: 15 ml) in which dextran sulfate was immobilized, and further 23 ml of RO water was added thereto. Then by conducting reaction at 45° C. for two hours, a ring-opening reaction (end-capping reaction) of unreacted epoxy groups was carried out to give an adsorbent (hereinafter referred to as "CKA80-DS"). An amount of immobilized dextran sulfate on this carrier was 2.09 mg/ml (sedimentation volume of gel).

A carrier for an adsorbent was prepared by using a water-insoluble carrier shown in Table 1 by the same method.

The production No. 5 was prepared in the following manner.

Ten milliliters of epoxidated styrene-divinylbenzene copolymer (POROS 50EP available from Perseptive Biosystems Incorporated, average particle size: 36 μm, not less than 80% by volume of particles have a particle size of within +20% of an average particle size, hereinafter referred to as POR-EP) in sedimentation volume was weighed. After 7.0 g of dextran sulfate and 5.0 ml of reverse osmosis water which were the same as used in CKA80-DS were dissolved completely, thereto was mixed the weighed POR-EP and then added 2M NaOH at room temperature to adjust pH of the mixture to 9.2. Then the mixture was stirred at 45° C. for 24 hours in a constant temperature water bath to carry out immobilization of dextran sulfate. Subsequently reverse osmosis water was added to 77 μl of monoethanolamine to give a solution having a total weight of 2.2 ml. This solution was added to 10 ml (sedimentation volume) of the gel in which dextran sulfate had been immobilized, and further 15.3 ml of reverse osmosis water was added thereto, followed by reacting at 45° C. for two hours to carry out an end-capping reaction of unreacted epoxy.

passed through the column by the following equation. The results (average of measurements made three times) are shown in Table 2. In any measurements, a percentage of erythrocytes having passed through the column was 100%.

TABLE 1

| | | Water-insoluble carrier | | | |
|---|---|---|---|---|---|
| Production No. | Symbols of product | Material | Average particle size ($\mu$m) | Particle size distribution[1] (%) | Immobilizing amount[2] (mg/ml) |
| 1 | CKA80-DS | Porous cellulose gel | 80 | ±10 | 2.09 |
| 2 | CKA200-DS | Porous cellulose gel | 200 | ±10 | 2.60 |
| 3 | CKA250-DS | Porous cellulose gel | 250 | ±10 | 2.27 |
| 4 | CKA350-DS | Porous cellulose gel | 350 | ±20 | 2.14 |
| 5 | POR-DS | Epoxidated styrene-divinylbenzene copolymer | 36 | ±20 | 2.26 |

[1]This indicates in what percentage of average particle size the particle size of particles amounting to not less than 80% by volume is.
[2]based on 1 ml of gel sedimentation volume.

EXAMPLE 2
(Adsorption experiment)

Dextran sulfate-immobilized porous cellulose gels of the production numbers 1 to 5 which were prepared in Example 1 were washed with a heparin-added physiological salt solution (adjusted so that a final heparin content became 7U/ml) to equilibrate heparin. After the defoaming of the gel, 1 ml of the gel in sedimentation volume was packed in a mini-column made of polypropylene (inner diameter: 9 mm, height: 16 mm, available from TERUMO Corporation). At the entry side of the column, a polyvinyl chloride tube (inner diameter: 1 mm, outer diameter: 3 mm, length: 1 m) was fitted and thus the mini-column with a blood circuit was produced.

Blood was collected with care from a healthy person by using heparin as an anticoagulant by means of a 18G injection needle. The collected blood was then put in an Erlenmeyer flask made of Teflon (inside volume: 100 ml, available from Sanwa Kabushiki Kaisha) which was then rotated at low speed with a stirrer tip in a constant temperature bath of 37° C., and passing of the blood was started at a flow rate of 0.5 ml/min.

A point when the blood flowed out from the exit side of the mini-column was assumed to be a starting time of passing blood. Afterwards every five minutes, a specified amount of blood at the exit side of the column was collected, and the number of hemocytes in blood (erythrocyte, leukocyte and platelet) was measured with a hemocyte counter (Microcell Counter CC-180, available from Sysmex Corporation) to calculate a percentage of hemocytes having $$\text{Percentage of passed hemocytes (\%)} = \frac{\text{Number of hemocytes at exit side of a column}}{\text{Number of hemocytes at collecting blood}} \times 100$$

For comparison, flow of blood was determined also with respect to a porous cellulose gel in which dextran sulfate was not immobilized. The results are shown in Table 2. Carriers having average particle sizes of 80 $\mu$m, 200 $\mu$m, 250 $\mu$m and 350 $\mu$m were abbreviated to CKA80, CKA200, CKA250 and CKA350, respectively. In these carriers, too, a percentage of erythrocytes having passed through the column was 100%.

TABLE 2

| | Percentage of passed hemocytes (%) | | | | | | | |
|---|---|---|---|---|---|---|---|---|
| | CKA 80-DS | CKA 80 | CKA 200-DS | CKA 200 | CKA 250-DS | CKA 250 | CKA 350-DS | CKA 350 |
| Leukocyte | | | | | | | | |
| 10 minutes after start of passing blood | 96 | 75 | 97 | 86 | 100 | 92 | 100 | 94 |
| 20 minutes after start of passing blood | 86 | 67 | 98 | 80 | 99 | 79 | 100 | 83 |
| 30 minutes after start of passing blood | 85 | 63 | 92 | 75 | 90 | 75 | 97 | 80 |
| Platelet | | | | | | | | |
| 10 minutes after start of passing blood | 48 | 38 | 65 | 51 | 58 | 47 | 59 | 53 |
| 20 minutes after start of passing blood | 73 | 36 | 75 | 47 | 82 | 42 | 83 | 49 |
| 30 minutes after start of passing blood | 78 | 78 | 92 | 77 | 90 | 84 | 91 | 76 |

As it is clear from Table 2, percentages of passed leukocytes were nearly 100% in any of CKA350-DS, CKA250-DS and CKA200-DS. In CKA80-DS, the percentage was about 90%. In CKA200-DS, CKA250-DS and CKA350-DS, there was almost no difference in a percentage of passed platelets. At an initial stage of passing blood, the percentage was about 50%, and then increased with a lapse of time and after 20 minutes from the starting of passing blood, showed a value of not less than 80%. Also in CKA80-DS, the percentage was about 40% at the time of starting of passing blood, and afterwards increased with a lapse of time and showed about 75% at the time when 30 minutes had elapsed for the completion of evaluation.

In case of gels in which dextran sulfate was not immobilized, percentages of passed leukocytes in any of CKA80, CKA200 CKA250 and CKA350 showed values 10to 20% lower than those of gels having corresponding particle sizes in which dextran sulfate was immobilized. On the other hand, percentages of passed platelets in case of gels in which dextran sulfate was not immobilized showed, in each particle size, values 10to 40% lower than those of gels in which dextran sulfate was immobilized.

EXAMPLE 3

By using the experiment system produced in Example 2, a blood coagulation time was measured in the same manner as in Example 2 after the blood having passed through a mini-column filled with dextran sulfate-immobilized gels having various particle sizes and prepared in Example 1, by means of a blood coagulation time meter (Blood Coagulation Analyzer CA-100 available from Sysmex Corporation). The blood coagulation time (of extrinsic pathway and intrinsic pathway) was measured by collecting a specified amount of blood at the exit side of the column every 10 minutes from the starting of passing blood, centrifuging at 3000 rpm for 15 minutes and then neutralizing heparin in plasma with protamine sulphate. For comparison, measurement was made also with respect to gels having each particle size in which dextran sulfate was not immobilized. The results (average of measurements made three times) are shown in Table 3.

blood, but was not recovered even in 30 minutes after the completion of evaluation.

On the contrary, in the gels in which dextran sulfate was not immobilized, any gels having various particle sizes maintained the blood coagulation times (both extrinsic pathway and intrinsic pathways) at the time of collecting blood, and almost no fluctuation was recognized.

EXAMPLE 4

The gel POR-DS prepared in Production No. 5 of Example 1 was washed with a physiological salt solution (previously adjusted so that a final heparin content became 7U/ml) having a volume of 20 times the gel sedimentation volume.

After putting the gel POR-DS in an amount of 0.5 ml per tube of sedimentation volume (sedimentation of gel was previously carried out at 800 rpm for 30 seconds) in a polypropylene test tube, a supernatant was removed and blood (7U/ml) anticoagulated with heparin was added in an amount of 3 ml per tube. Then after sealing with a cap, shaking was carried out 60 times/min at 37° C. for 30 minutes.

Thirty minutes after starting of the shaking, by measuring the number of platelets existing in blood, a ratio of the platelets which were not adhered to the gel (percentage of

TABLE 3

|  | CKA 80-DS | CKA 80 | CKA 200-DS | CKA 200 | CKA 250-DS | CKA 250 | CKA 350-DS | CKA 350 |
|---|---|---|---|---|---|---|---|---|
| Coagulation time of extrinsic pathway (sec) | | | | | | | | |
| (at collecting blood) | (20) | (20) | (20) | (20) | (20) | (20) | (20) | (20) |
| 10 minutes after start of passing blood | 54 | 20 | 25 | 20 | 25 | 23 | 24 | 24 |
| 20 minutes after start of passing blood | 27 | 16 | 21 | 19 | 23 | 23 | 21 | 23 |
| 30 minutes after start of passing blood | 24 | 18 | 20 | 19 | 23 | 24 | 22 | 23 |
| Coagulation time of intrinsic pathway (sec) | | | | | | | | |
| (at collecting blood) | (82) | (82) | (82) | (82) | (82) | (82) | (82) | (82) |
| 10 minutes after start of passing blood | 2905 | 76 | 1393 | 76 | 588 | 96 | 396 | 100 |
| 20 minutes after start of passing blood | 1688 | 82 | 459 | 72 | 433 | 98 | 280 | 96 |
| 30 minutes after start of passing blood | 1016 | 68 | 368 | 75 | 278 | 95 | 268 | 95 |

The coagulation time of an extrinsic pathway (prothrombin time) maintained a value at the time of collecting blood and showed no change in case of CKA350-DS and CKA250-DS, but in CKA200-DS, showed a slightly extending tendency 10 minutes after starting of passing blood. Further in CKA80-DS, 10 minutes after starting of passing blood, the coagulation time showed a value about three times that at the time of collecting blood. Afterwards the coagulation time of an extrinsic pathway showed a remarkably recovering tendency, and at the time of completion of blood passing treatment, there was recognized almost no difference in the coagulation time among the gels having different particle sizes.

The coagulation time of an intrinsic pathway (activated partial thromboplastin time) showed remarkable extension at the evaluation time of 10 minutes and 20 minutes after passing of blood with respect to the gels having any particle sizes. With a lapse of time, the coagulation time showed a tendency of approaching to a value at the time of collecting non-adhered platelets) was calculated by the following equation. After this sample was centrifuged at 3000 rpm for 15 minutes, a supernatant was collected in an amount of 0.5 ml, heparin was neutralized with protamine sulphate and a blood coagulation time (intrinsic and extrinsic pathways) was measured in the same manner as in Example 3. For comparison, measurement was made similarly with respect to the material POR-EP in which dextran sulfate was not immobilized. The results (average of measurements made two times) are shown in Table 4.

Percentage of non-adhered platelets (%) =

$$\frac{\text{Number of platelets in blood in which sample gel is added}}{\text{Number of platelets in blood in which gel is not added}} \times 100$$

TABLE 4

|  | Percentage of non-adhered platelets (%) | Coagulation time of extrinsic pathway (sec) | Coagulation time of intrinsic pathway (sec) |
| --- | --- | --- | --- |
| At collecting blood | — | 18 | 90 |
| POR-EP | 57 | 21 | 84 |
| POR-DS | 70 | 58 | 1945 |

As it is clear from Table 4, a percentage of non-adhered platelets to POR-DS was as high as 70%. With respect to the blood coagulation time, the coagulation time of the extrinsic pathway was extended to about three times the value at collecting blood, and the coagulation time of the intrinsic pathway was extended to about twenty times the value at collecting blood.

On the other hand, with respect to POR-EP in which dextran sulfate was not immobilized, a ratio of platelets which were not adhered to a gel (percentage of non-adhered platelets) was as low as about 57% as compared with control in the case of adding no gel. The blood coagulation time of both extrinsic and intrinsic pathways maintained values at collecting blood, and a large fluctuation was not recognized.

INDUSTRIAL APPLICABILITY

By using the method of the present invention, it becomes possible to inhibit adhesion of luekocytes and platelets to a large extent and largely extend a blood coagulation time, and as a result, it becomes possible to further minimize a particle size of a water-insoluble carrier used for direct hemoperfusion, thus making it possible to achieve both increase in adsorption volume and enhancement of flow of blood in the direct hemoperfusion.

What is claimed is:

1. An adsorbent which is used for direct hemoperfusion and is prepared by immobilizing, on a water-insoluble carrier, (i) a sulfated polysaccharide and/or its salt and (ii) a ligand which adsorbs a specific substance during hemoperfusion and is different from the sulfated polysaccharide and/or its salt.

2. An adsorbent which is used for direct hemoperfusion and is prepared by immobilizing, on a water-insoluble carrier, (i) a sulfated polysaccharide and/or its salt having a limiting viscosity of not less than 0.005 dl/g and not more than 0.5 dl/g and a sulfur content of not less than 5% by weight and not more than 22% by weight, and (ii) a ligand which adsorbs a specific substance during hemoperfusion and is different from the sulfated polysaccharide and/or its salt.

3. The adsorbent of claim 1, wherein the sulfated polysaccharide and/or its salt is immobilized on the water-insoluble carrier in an amount of not less than 0.02 mg and not more than 200 mg per 1 ml of the water-insoluble carrier.

4. The adsorbent of any of claim 1, wherein an average particle size of the water-insoluble carrier is not less than 30 µm.

5. The adsorbent of claim 2, wherein the sulfated polysaccharide and/or its salt is immobilized on the water-insoluble carrier in an amount of not less than 0.02 mg and not more than 200 mg per 1 ml of the water-insoluble carrier.

6. The adsorbent of claim 2, wherein an average particle size of the water-insoluble carrier is not less than 30 µm.

7. The adsorbent of claim 5, wherein an average particle size of the water-insoluble carrier is not less than 30 µm.

8. The adsorbent of claim 5, wherein an average particle size of the water-insoluble carrier is not less than 30 µm.

9. A method for treating blood, comprising contacting blood with an adsorbent as claimed in claim 1.

10. A method for preparing an adsorbent which is used for direct hemoperfusion, comprising immobilizing, on a water-insoluble carrier, (i) a sulfated polysaccharide and/or its salt and (ii) a ligand which adsorbs a specific substance during hemoperfusion and is different from the sulfated polysaccharide and/or its salt.

11. The method for preparing an adsorbent of claim 10, wherein the sulfated polysaccharide and/or its salt is immobilized on the water-insoluble carrier in an amount of not less than 0.02 mg and not more than 200 mg per 1 ml of the water-insoluble carrier.

12. A method for preparing an adsorbent which is used for direct hemoperfusion, comprising immobilizing, on a water-insoluble carrier, (i) a sulfated polysaccharide and/or its salt having a limiting viscosity of not less than 0.005 dl/g and not more than 0.5 dl/g and a sulfur content of not less than 5% by weight and not more than 22% by weight, and (ii) a ligand which adsorbs a specific substance during hemoperfusion and is different from the sulfated polysaccharide and/or its salt.

13. The method for preparing an adsorbent of claim 12, wherein the sulfated polysaccharide and/or its salt is immobilized on the water-insoluble carrier in an amount of not less than 0.02 mg and not more than 200 mg per 1 ml of the water-insoluble carrier.

* * * * *